United States Patent [19]

Alagy et al.

[11] Patent Number: 4,971,770
[45] Date of Patent: Nov. 20, 1990

[54] PROCESS INVOLVING OXIDATION REACTOR USED OXIDIZE A GASEOUS PHASE OXIDIZABLE FEED

[75] Inventors: Jacques Alagy, Charbonnieres les Bains; Christian Busson, Dardilly, both of France

[73] Assignee: Institut Francais du Petrole, Rueil Malmaison, France

[21] Appl. No.: 264,393

[22] Filed: Oct. 31, 1988

Related U.S. Application Data

[63] Continuation of Ser. No. 920,188, Oct. 17, 1986, abandoned.

[30] Foreign Application Priority Data

Nov. 17, 1985 [FR] France ................................ 85 15550
Dec. 30, 1985 [FR] France ................................ 85 19427

[51] Int. Cl.$^5$ .............................................. B01J 8/04
[52] U.S. Cl. .................................. 422/191; 48/198.6; 48/198.7; 422/190
[58] Field of Search ............. 422/190, 191; 48/196 R, 48/198.6, 198.7, 198.8

[56] References Cited

U.S. PATENT DOCUMENTS 3,208,833 9/1965 Carson ................................. 422/191

Primary Examiner—Robert J. Warden
Assistant Examiner—Jill Johnston
Attorney, Agent, or Firm—Antonelli, Terry, Stout & Kraus

[57] ABSTRACT

A new technique for oxidizing a gaseous phase oxidizable feed involves a process wherein a gas mixture containing at least one oxidizing gas is placed in contact with an oxidizable feed inside a mixing contact zone situated between at least one first zone passed through by the feed and at least one second zone passed through by the oxidation reaction products. The first and second zones define a multiplicity of multidirectional spaces exhibiting passages having, along at least one direction, a dimension at most equal to the jamming distance of the flame possibly resulting from oxidations of feed. The contact zone comprises an oxidizing gas mixture supply means comprising a plurality of parallel pipes with porous walls situated at a distance from the first and second zones which is at most equal to the jamming distance.

3 Claims, 3 Drawing Sheets

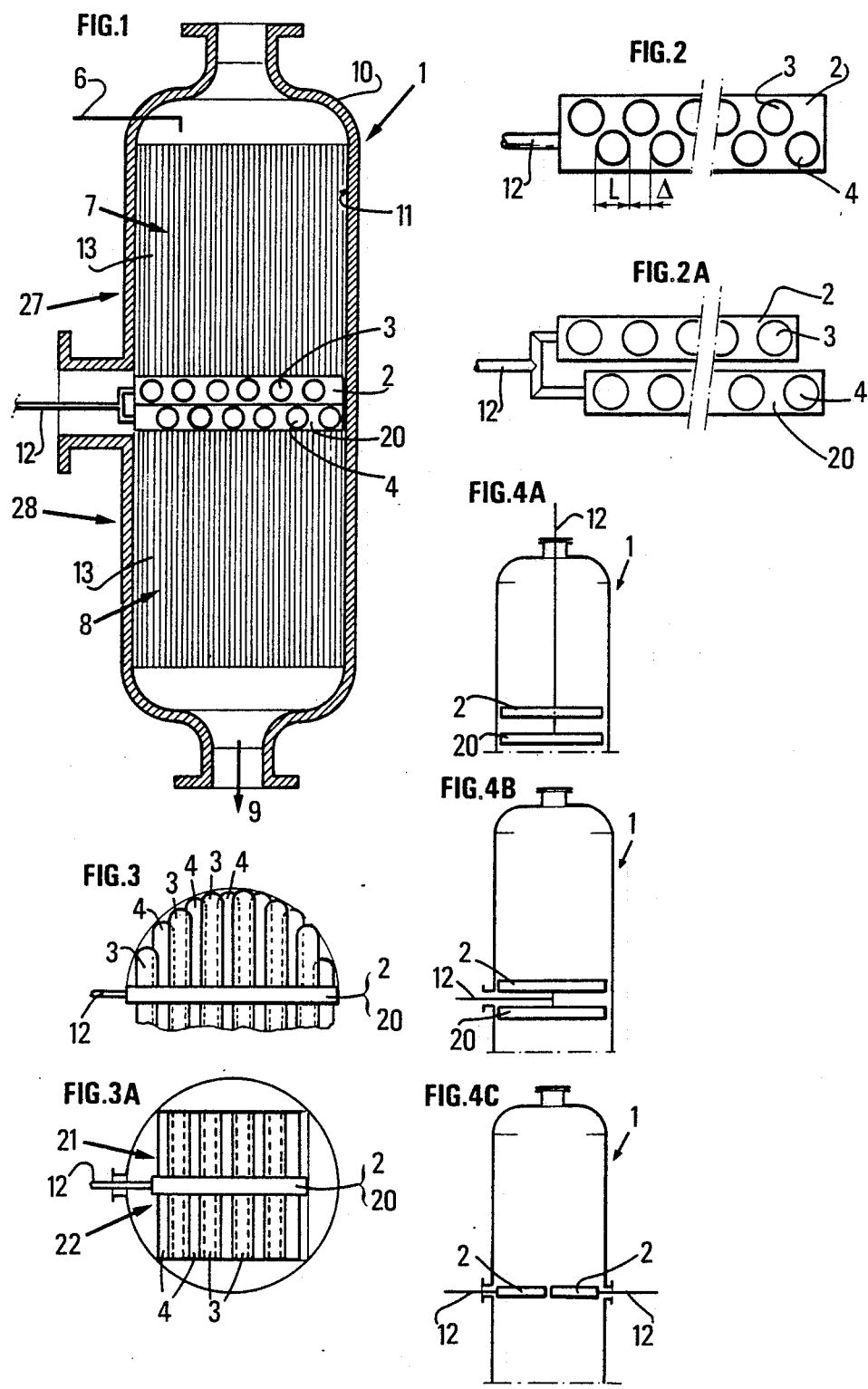

PROCESS INVOLVING OXIDATION REACTOR USED OXIDIZE A GASEOUS PHASE OXIDIZABLE FEED

This is a continuation application of U.S. Ser. No. 920,188, filed Oct. 17, 1986 now abandoned.

The present invention concerns a new reactor, its use and a process for oxidizing a gaseous phase oxidizable feed by means of a gas mixture containing at least one oxidizing gas.

The present invention is directed particularly to the slow or partial oxidation of oxidizable feeds, such as, for example, hydrocarbons with a view to the preparation of synthesis gas mainly comprising carbon monoxide and hydrogen, for example for the synthesis of methanol and homologous high-grade alcohols. The invention can also be used, for example, for the oxidation of vapour-reforming effluent, benzene, or in ammonoxidation reactions.

Although oxidizing gases are usually oxygen, ozone or halogens, only the reactions with oxygen shall be considered by way of example hereinafter.

A method for partially oxidizing methane is already known, as indicated in the patent US-2,621,117, for example.

The reaction occurs in a flame where the mixture of gases is never perfect. In these conditions, high temperatures are quickly reached in the zones rich in oxygen.

The high temperature gas products are then mixed in an on-feed rIch zone to be oxidized. Such conditions provoke the cracking of molecules with the formation of carbon likely, for example, to provide dirty catalysts during the process and thus reduce the efficiency of the reaction.

Where methane is involved, carbon is produced and the synthesis gases must subsequently be freed from dust prior to being used, for example for the synthesis of methanol from carbon monoxide and hydrogen.

Apart from the formation of carbon black, excessive overheating may be produced in the zone where the contact of reaction gases is being carried out and, in a large number of cases, these undesirable effects can usually be attributed to the device for mixing reaction gases at the reactor input, the gases being mixed at a speed which is too slow in relation to the gaseous phase reaction speed.

This type of mixing occurs when oxygen is injected through a single channel which, moreover, must have a section sufficiently large to admit the whole flow and although the gas is injected at high speed through this section, the speed at which the oxygen molecules are dispersed is slow compared with the reaction speed.

Furthermore, the oxygen jet at the place where the jet leaves an opening is generally in the environment of the gas to be oxidized which circulates at low speed inside the reactor and which does not favour a rapid dispersion of oxygen molecules.

The prior art is particularly illustrated by patents DE-A-1.1.804. 093 and FR-A-1.395.256.

According to the patent US-2,772,149, the reaction gases are mixed on the surface of a low surface area porous diaphragm where oxygen and hydroCarbons are injected in the same direction. This offers the advantage of the reaction gases being able to be mixed quickly.

However, owing to the slow speed of the gas passing through the pores of the diaphragm, the reaction takes place mainly on the outlet surface of the diaphragm which must accordingly be designed so as to be able to resist high temperatures. In high capacity units, this device would require the diaphragm to have a large surface area which renders the process impractical.

EU-0.001.946 describes a reactor where oxygen, owing to its high flowrate, is injected into the process gas through a large number of parallel channels each terminating in an outlet, at least one of whose dimensions is greatly reduced, such an outlet being a slot, the width of which is preferably less than 8 mm.

Furthermore, so as to increase the dispersion speed of the oxygen inside the process gas, the process gas is propelled by a vigorous helicoidal movement around the channels obtained by this gas being tangentially injected onto the internal walls of the device.

In addition, it is widely known, as in particular described in the book by G. de Soete and A. Feugier and entitled "Physical and chemical aspects of combustion",* that the reaction speed can be reduced by using the "wall" effect and propagation of the flame can thus be avoided.
Editions Technip, pages 87 to 93

In the present case, the presence of pure oxygen and a high temperature involving a high thermal flux necessitate the use of flame arrester devices enabling the reaction to be continued without the risk of explosion, if not, the explosive conditions would be reached (especially in the case of partial oxidation of methane).

The objects which solve the problems posed by the prior art are essentially the following:

an oxygen and on-feed distribution adapted to provide a fully controlled quasi-homogeneous mixture of oxygen and the feed to be oxidized. This distribution must be particularly suitable for the rapid dispersion of oxygen molecules.

a "flame stoppage or jamming" avoiding the risk of explosion yet enabling operation to take place at temperatures of more than 1,000° C. and capable of protecting the reactor and mixing device from the excessive heat emitted during partial oxidation.

The present invention offers a new process overcoming the drawbacks of the prior art. More particularly, it concerns a process for oxidizing a gaseous phase oxidizable feed by means of a gas mixture containing at least one oxidizing gas in which the reaction products are collected.

More precisely, the gas mixture and oxidizable feed are placed in contact inside a mixing contact zone or chamber situated between at least one first zone passed through by said feed and at least one second zone or chamber passed through by the oxidation products obtained from the contact zone, said first and second zones defining a multiplicity of multidirectional spaces exhibiting passages having, along at least one direction, one dimension at the most equal to 10 millimetres and corresponding to the flame jamming or stopping distance possibly resulting from oxidation of said feed, said contact zone comprising an oxidizing mixture supply zone which comprises a plurality of roughly parallel pipes with porous walls and that is situated at a distance from the first and second zones which is at the most equal to the jamming distance.

The spaces in the first and second zones are advantageously situated in the immediate vicinity of the contact zone.

The invention also concerns a reactor for implementing the process.

This reactor comprises oxidizable on-feed and oxidizing gas supply means and means for evacuating the reaction products. In addition, it comprises in combination:

at least one oxidizing gas distributor connected firstly to the oxidizing gas supply means and secondly to a plurality of roughly parallel pipes with ceramic porous walls, at least one first zone or chamber containing a ceramic packing which defines a multiplicity of multidirectional spaces exhibiting passages having, along at least one direction, one dimension at the most equal to 10 mm, this dimension corresponding to the jamming distance of the flame which might result from oxidation of said feed, said first zone or chamber being connected to said oxidizable on-feed supply means, and at least one second zone or chamber containing a ceramic packing which defines a multiplicity of multidirectional spaces exhibiting passages having, along at least one direction, one dimension at the most equal to 10 mm, this dimension corresponding to the jamming distance of the flame which might result from oxidation of said feed, said second zone being connected to said means for evacuating reaction products, said first and second zones being situated on both sides of said porous pipes at a distance which at the maximum is equal to the jamming distance.

It is advantageous that said distance be between 0.05 mm and 10 mm and preferably it should be between 0.1 mm and 5 mm.

The entire surface of the pipes is advantageously porous.

The spaces relating to the first and second zones have said one dimension advantageously of between 0.1 mm and 5 mm.

Preferably, the space thus supplied is uniform.

Having regard to the thermal levels attained (e g. 1,400° C. for the partial oxidation of methane) and the presence of preferably pure oxygen, said feed and reaction products inside the spaces surrounded by ceramic walls and said oxidizing mixture inside channels whose walls are ceramic are drained off.

It is possible to use as refractory materials ceramics such as mullite, silicon carbide, cordierite, silicate of alumina, silicon nitrides such as $Si_3N_4$, alkaline-earth oxides, the oxides of transition metals and their compounds.

Silicon carbide is preferably selected as it offers good thermal conductivity and thus favours increased temperature uniformity. Moreover, as this material is easily extrudable, it is much easier to implement such assemblies.

Each chamber (the first or the second) has, close to the pipes with porous walls, a yield surface roughly equal to that occupied by these pipes. Firstly, the yield surfaces of the feed and secondly those of the reaction products are preferably roughly opposite the surface area actually occupied by the porous pipes with the result that there is correspondence of the gas flows.

Thus, for example, opposite the oxidizing gas distributor which is not porous, are zones corresponding to the first and second chambers blocked by a baked ceramic paste and inside which there is no flow.

The distrbutor comprises a feed pipe on which are fixed several porous pipes which, according to one mode of embodiment, entirely cover at least one part of the reactor section which faces the capacities and their packing. Good results have been obtained when the section covered by these porous pipes is approximately perpendicular to the axis of the reactor and thus to the direction of the feed flow. However, the section covered by the pipes, instead of being straight, may be roughly oblique and therefore slanting in relation to the plane roughly perpendicular to the reactor axis.

The porous pipes may be disposed in non-adjacent offset layers on both sides of the distributor on a given plane so as to facilitate flux flow.

A particularly advantageous case is where the reactor comprises two oxidizing gas distributors, each of these being connected to a multiplicity of porous-walled pipes roughly parallel and thus defining a first and second layer of pipes which are offset without touching each other. This disposition allows for greater control, especially thermal control, whilst permitting flux flow. The distance between two pipes in a given radial plane of a given layer is at the maximum equal to the width of a pipe.

When the oxidizing mixture pipes, for example of oxygen, are adjacent, at least one of them may be pierced by a plurality of holes on both sides of a longitudinal plane passing through its axis, these holes having one dimension between 0.05 mm and 10 mm (jamming distance) so as to permit flux flow and "jamming" of the flame.

Where a single distributor is involved, the upper edge of the pipes of the lower row is higher than the lower edge of the pipes of the upper row.

The width of each porous pipe varies according to the size of the reactor. For example, it is between approximately 5 and 10 mm and preferably between about 10 and 20 mm.

The length of each porous pipe is selected according to an embodiment mode so that the total section of the reactor is completely covered by the pipes, irrespective of the geometry of the reactor. In the case of a roughly cylindrical reactor with a circular cross section, the length of the roughly parallel porous wall pipes is inscribed inside a circle coaxial to the circle defined by the circular sectIon of the internal wall of the reactor.

However, if the pipes are inside another plane exhibiting a slant in relation to the plane roughly perpendicular to the axis of the reactor, the length of these pipes is inscribed inside the ellipse defined by the section of the cylindrical reactor by the plane of the pipes.

A highly uniform layer of oxygen is thus created over the whole effective section of the reactor, this layer being scavenged by the feed to be oxidized, itself being uniformly distributed as described subsequently, which favours a micromixture inside the confined zone between the capacities and the oxygen pipes and a rapid dispersion.

Porosity is selected so that for a given flow, the loss of pressure will be sufficient to ensure that all the porous pipes are fed with oxygen by the distributor.

Preferably, a loss of pressure of between 0.05 and 10 bars is chosen, without this choice being restrictive.

The packing may include at least one monolith filling each of the capacities. This monolith comprises a plurality of channels juxtaposed preferably roughly parallel to each other and to the axis of the reactor; the section of each channel is included between $0.0025$ $mm^2$ and $100$ $mm^2$ and preferably between $0.1$ $mm^2$ and $20$ $mm^2$. The surface area of each channel is preferably roughly the same.

This solution offers the advantage of the feed being distributed homogeneously according to the axis of the monolith.

According to another mode of embodiment, the packing may include particulate ceramic elements, for example in the form of balls and rods between 0.01 mm and 10 mm in size and preferably between 0.1 mm and 5 mm.

Preferably, balls are used which, when placed in contact, offer a maximum length space at the most equal to their radius, which enables the size of these balls to be selected according to the desired jamming distance.

In such conditions, the spaces defined by the particulate elements are all the smaller due to the particulate elements having, for example, smaller dimensions. It is then possible to proceed with stoichiometric and under pressure oxidation reactIons in the presence of almost pure oxygen, which necessitates that flame jamming distances be extremely short, which the monolith technology may only reach with difficulty.

Indeed, it is difficult to produce a very small unit section monolith which requires careful handling at the time of loading and unloading.

Moreover, the presence of the packing in the form of particulate elements facilitates the loading and unloading operations inside the capacities and the regeneration of these particles by calcination of the carbon deposited or by chemical means (acid, for example), especially if heavy feeds containing metals such as nickel and vanadium are being treated.

According to another mode of embodiment, at least one of the passage containing chambers contains a packing comprising at least one monolith which includes a plurality of channels juxtaposed, preferably roughly parallel to each other and the axis of the reactor. These channels may generally have a surface area of between approximately 0.025 mm$^2$ and 100 mm$^2$, but they may also have a larger surface area of up to 25 cm$^2$ for example, which enables at least one of the capacities to be compartmentalized.

In addition, in the two cases mentioned above, at least one of these channels comprises, at least partly, a filling in the form of particulate ceramic elements whose size is between 0.01 mm and 10 mm and preferably between 0.1 mm and 5 mm. In this way, the oxidizable feed is properly channelled which allows for a roughly uniform distribution of this feed at the level of the oxidizing gas distributor and a regular flow over the whole of the section of the reactor, as in this case there is no possibility of preferential currents. Generally, the particulate elements may include a catalyst.

The particles may be any shape, regular or irregular. Alone, the spaces defined between their walls are important, the size of the particles and especially the diameter of the balls being selected according to this parameter.

For example, the length of the first and second zones or chamber or of each unit channel, in a case of a monolith, is from 10 mm to 3,000 mm. Preferably, the length of the capacity upstream of the contact zone with oxygen may be smaller than that of the downstream capacity and equal to from 20 mm to 500 mm as regards the first and from 100 mm to 2,000 mm as regards the second.

Before arriving at the oxygen distrIbutor, the feed to be oxidized, in the gaseous state, is channelled and flows roughly along the axis of the reactor due to the packing of the first capacity, one of whose extremities is opposite the distributor.

The section of spaces (for example, of channels in the case of monoliths) and pipes can take at least one of the following shapes which are not restrictive: polygonal, square, rectangular, cylindrical, elliptic, circular or triangular. In the case of monoliths, the unit channel section is preferably square.

The gaseous feed circulates, for example, roughly from bottom to top or from top to bottom in the case of a vertical reactor and, in the confined zone between the packing and the porous pipes, comes into contact with the oxygen.

To this effect, the monolith(s) upstream (first) and downstream (second) of the oxygen distributor is/are hollowed out so that a preferably uniform space is provided between the porous pipes and the first and second monoliths with a depth equal at the maximum to 10 mm (flame jamming distance) and preferably from 0.1 mm to 5 mm, this space defining a set of cavities roughly parallel to the porous pipes.

The feed thus introduced is as close as possible to the porous oxygen distributor pipes to the extent that the open extremity of the monoliths fits these pipes exactly. The same applies to the particles which may even be in direct contact with the oxygen pipes so that, for example, the diameter of the balls is compatible with the flame jamming distance.

Thanks to the device, the feed to be oxidized is uniformly distributed over the whole section of the capacity at the level of the oxygen distributor without there being any retromixture. Secondly, owing to the small section of spaces, the risk of explosion is avoided (or backfire), thanks to the flame jamming phenomenon.

After being homogeneously mixed with oxygen, the reaction products are again channelled with the aid of at least one second capacity comprising a multiplicity of spaces with the above-defined shape and section.

The feeds to be treated have a residence time in the reaction zone of between 2 ms and 10,000 ms and preferably of between 50 ms and 1,000 ms.

BRIEF DESCRIPTION OF THE DRAWINGS

The invention will be better understood from the following description of several modes of embodiment, given by way of illustration by no means restrictive, supported by the annexed figures:

FIG. 1 represents the reactor according to the invention and shows an axial section, FIGS. 2 and 2A show a side projection of the oxygen supply with one distributor (FIG. 2) or two distributors (FIG. 2A), FIGS. 3 and 3A illustrate a top view of this supply, FIGS. 4A, 4B and 4C represent oxygen admission modes.

According to one mode of embodiment, FIG. 1 shows an extended cylindrical vertical reactor 1 comprising two oxygen distributors 2 and 20, each of which is connected to a layer consisting of a plurality of mullite pipes 3 and 4, roughly parallel and porous over their entire surface, each pipe having a, for example, a circular cross-section of 1 cm in diameter.

Figure 5:
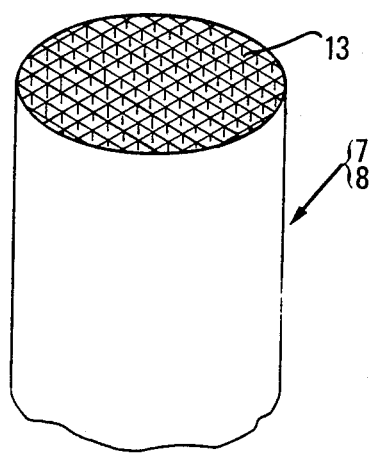
FIGS. 5 and 5A show a honeycombed monolith structure.

The porous surface seen from above is roughly that of a square geometric figure (FIG. 3A) divided into two approximately equal semi-rectangles 21 and 22 by the oxygen distributor 2.

The porous surface thus offered to the feed is about $100^2$ cm and the porosity is selected so that the pressure loss is roughly equal to 0.5 bar.

The distributor and porous pipes thus supplied by a line 12 are disposed roughly perpendicular to the axis of the reactor in a zone roughly upstream in relation to the radial plane of the reactor. The two layers 3 and 4 are alternate and non adjacent on both sides of the distributor, as shown by FIGS. 2 and 2A.

The distance Δ between two porous pipes of a given layer permitting flux flow is at the most equal to the width L of the pipes, namely 1 cm, and the distance between the two layers is about 6 cm.

According to FIG. 3 illustrating another mode of embodiment, the porous pipes roughly cover the whole section of the reactor by alternate offset non-adjacent layers of pipes 3 and 4 disposed on both sides of the oxygen distributor 2.

The length of each pipe is selected so that its extremity is roughly tangential to the circle corresponding to the section of the reactor, a circle whose diameter is roughly equal to that of the inside of the reactor in which the distributor is installed.

Oxygen can be supplied through a line 12 connected, for example, to the distributors 2 and 20 along the axis of the reactor (FIG. 4A) or laterally (FIG. 4B), or even with two semi-distributors (FIG. 4C), without such modes of embodiment being restrictive.

The gaseous oxidizable feed, previously preheated to 450° C., arrives through a pipe 6 and supplies from top to bottom a first zone or chamber 27 comprising a first monolith 7 whose length is approximately equal to 20 cm and which includes a plurality of mullite channels 13 juxtaposed roughly parallel to each other and the axis of the reactor.

This structure is similar to that of a honeycomb (FIG. 5), the whole section of which would be circular.

Figure 5A:
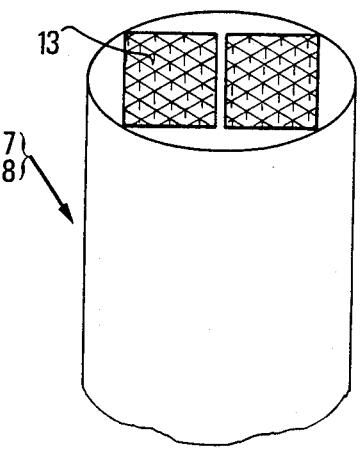

In the present case, the whole surface through which the load flows roughly corresponds to the porous surface from which the oxygen escapes. To this effect, as FIG. 5A shows, a baked ceramic paste blocks those parts of the monolith not opposite the oxygen distribution zone, for example the central zone of the distributor 2 or 20. Consequently, the surface area reserved for the flow is roughly the same as that from which the oxygen escapes, namely about 100 cm².

Each of the section channels equal to 1 mm² channels the feed so as to be roughly parallel to the axis of the reactor and distributes it uniformly inside the confined space between the oxygen distribution pipes 3 and 4 and the monolith 7 and a second monolith 8 situated under these pipes.

This space is roughly equal to 1 mm. In these conditions, retromixture phenomena are minimized.

The gaseous fluids flow between the porous pipes.

On the other side of the oxygen distributor is a second zone or chamber 28 comprising a monolith 8 which includes a plurality of parallel juxtaposed silicon carbide channels also parallel to the axis of the reactor, the first and second monoliths being perpendicular to the radial plane containing the porous oxygen supply pipes.

Their individual square section is about 1 mm² and the length of each channel is about 60 cm.

These channels are firstly designed to channel the reaction products as far as a product evacuation line 9 and secondly, owing to their narrow width and the wall effect, are designed to "jam the flame" which enables the reaction to be continued without the risk of explosion.

Figure 6:
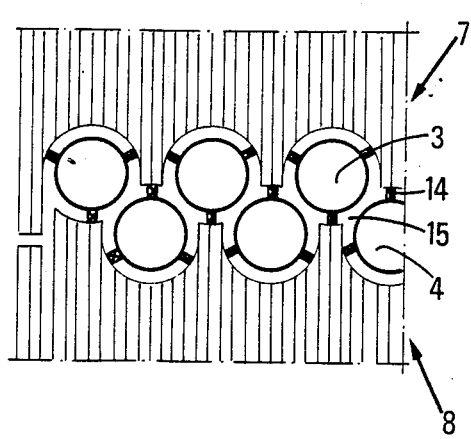
FIGS. 6 and 6A represent a detailed view of the oxygen supply (single or double) close to the upstream and downstream monoliths.
Figure 6A:
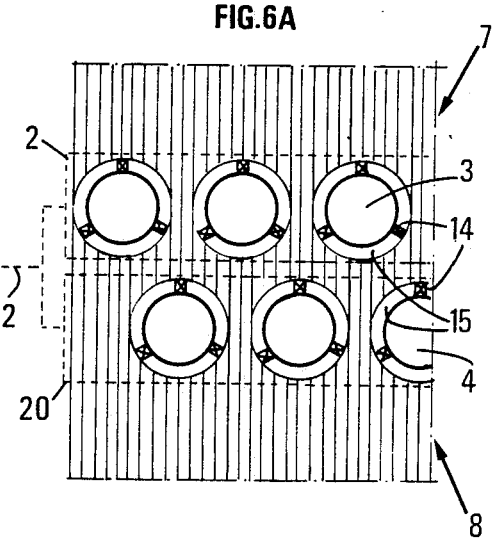

In practice, it is possible to have two monolith half-shells hollowed out on both sides of the oxygen distribution zone so that a set of uniform cavities 15 (FIGS. 6 and 6A) is provided, these cavities being parallel to each other and to the porous pipes and perpendicular to the channels 13 of the monoliths 7 and 8 and having dimensions which correspond to the jamming distance.

The half-shells are then assembled and the unit (monoliths and oxygen distributors) is kept in place by means of, for example, ceramic shims 14 inside a steel hoop 10, the unit being conventionally protected by concrete and/or refractory concrete layers 11 or insulating fireproof bricks in accordance with the recognized rules of the art when operating at high temperatures and under pressure.

Thanks to this disposition and the materials used, it is possible to produce oxidation reactions at very high temperatures, i.e; in the order of 1,300° C., without any carbon deposit occurring and with dwell times in the reactor not exceeding 1,000 ms.

For example, through the line 6, an oxidizable feed is introduced comprising methane and steam preheated to about 450° C. in a mol ratio $H_2O/CH_4$ equal to about 0.8. 0.55 mols of oxygen are introduced through line 12 at a temperature of about 150° C.

The $O_2/CH_4$ mol ratios which are recommended, for example 0.5 to 0.75 and in this example 0.55, may enable a synthesis gas to be obtained whose $H_2/CO$ mol ratio is, for example, close to 2 with a gas outlet temperature of about 1,080° C., the reactor being at a pressure of about 20 bars.

It is quite obvious that the admission level of the feed and the drawing off level of the reaction products are selected indiscriminately in the high or low position on the reactor.

Figure 7:
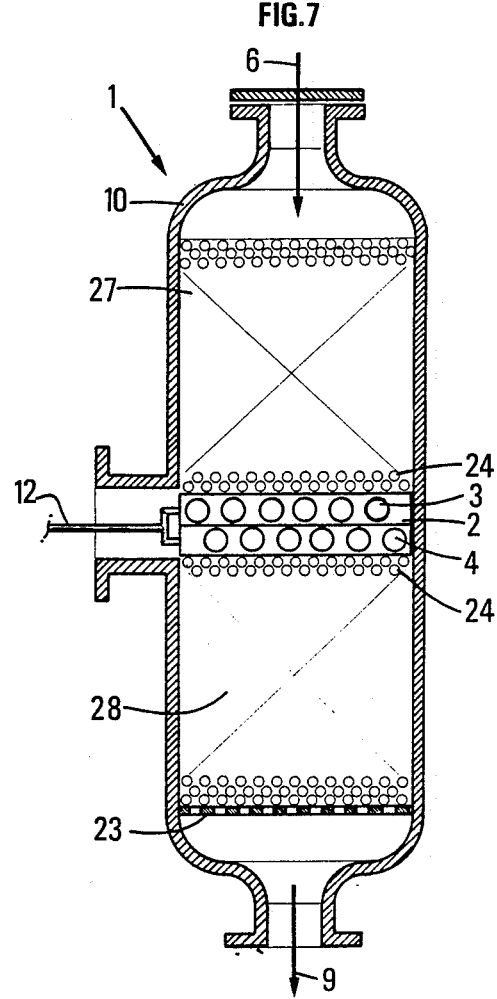
FIG. 7 illustrates another mode of embodiment of the reactor with chambers including a packing of particulate elements.

According to another mode of embodiment illustrated by FIG. 7, the reactor 1, such as the one described in FIG. 1, contains a first zone 27 and a second zone 28 disposed on both sides of the oxygen distributors 2 and 20 whose length is roughly equal to the diameter of the reactor, namely 10 cm.

In this case, the zones or chambers are filled with silicon carbide balls 24 which are spherically shaped and have a diameter of 0.5 mm selected according to the flame jamming distance.

The balls adhere to the oxygen distributors in such a way that the spaces defined between firstly the walls of the balls and secondly between the distributor and the point of contact of the balls is at the maximum equal to the radius of the balls (0.25 mm) which becomes the flame jamming distance.

The height of the packing 27 upstream of the distributors 2 and 20 is, for example, about 0.40 m, whilst the height of that situated downstream and which constitutes the actual reaction zone 28 is about 1 m.

A grate 23 keeps the packing in position.

The example which follows is given by way of illustration.

In this ball reactor operating under 80 bars, an oxidizable feed is introduced through line 6, this feed comprising methane and steam preheated to 400° C. in a mol ratio where $H_2O/CH_4$ is equal to 1.04.

Oxygen, in a mol ratio of $O_2/CH_4$ equal to 0.66, is introduced at a temperature of about 150° C. by the line 12.

Following the reaction, the gases have a temperature of 1,190° C. and the following composition (mol %):
$CH_4$ : 0.30%
CO : 19.8%
$H_2$ : 44.7%
$CO_2$ : 5.8%
$H_2O$ : 29.3%

Within the framework of the present invention, it is possible to build, for example, a reactor comprising, as regards the first zone, at least one monolith and one particulate element filling, and a second zone comprising a packing of particulate elements, or vice versa.

We claim:

1. A process in which flammable reaction products are produced in a reactor, wherein a gaseous phase oxidizable feed is oxidized with a gas mixture containing at least one oxidizing gas in a contact and mixing zone of the reactor, which comprises passing the gaseous phase oxidizable feed through at least one zone, arranged prior to said contact and mixing zone, within the reactor; contacting said gas mixture and said oxidizable feed within the contact and mixing zone to produce reaction products; and passing said reaction products through at least one second zone of the reactor; said contact and mixing zone being situated between said at least one first zone passed through by said feed and said at least one second zone passed through by the reaction products, said first and second zones including a filling material providing a multiplicity of multi-directional spaces forming passages for allowing flow of gas with low pressure drop therebetween and having in any one direction a dimension not exceeding a distance for stopping a flame which may result from oxidation of said feed, said flame stopping distance not exceeding 10 mm., said contact and mixing zone including an oxidizing gas mixture supply means comprising a plurality of substantially parallel pipes with porous walls that are situated at a distance from the first and second zones which is at most equal to said flame stopping distance.

2. The process according to claim 1, wherein said feed, said reaction products and said oxidizing gas are made to flow along ceramic walls of, respectively, said first zone, said second zone and said pipes.

3. The process according to claim 1 for the synthesis of methanol and high-grade homologous alcohols wherein said feed comprises a mixture of hydrogen and carbon oxides.

* * * * *